United States Patent
Sykes

(10) Patent No.: US 10,987,441 B1
(45) Date of Patent: Apr. 27, 2021

(54) DISINFECTING UVC LAMP APPLIANCE

(71) Applicant: William G. Sykes, Virginia Beach, VA (US)

(72) Inventor: William G. Sykes, Virginia Beach, VA (US)

(*) Notice: Subject to any disclaimer, the term of this patent is extended or adjusted under 35 U.S.C. 154(b) by 0 days.

(21) Appl. No.: 17/019,226

(22) Filed: Sep. 12, 2020

Related U.S. Application Data

(60) Provisional application No. 63/030,981, filed on May 28, 2020.

(51) Int. Cl.
  *A61L 2/10* (2006.01)
  *A61L 2/26* (2006.01)

(52) U.S. Cl.
  CPC .............. *A61L 2/10* (2013.01); *A61L 2/26* (2013.01); *A61L 2202/11* (2013.01); *A61L 2202/123* (2013.01); *A61L 2202/14* (2013.01); *A61L 2202/16* (2013.01); *A61L 2202/20* (2013.01)

(58) Field of Classification Search
  CPC .......... A61L 2/10; A61L 2/26; A61L 2202/14; A61L 2202/16; A61L 2202/20
  See application file for complete search history.

(56) References Cited

U.S. PATENT DOCUMENTS

| 3,843,521 A * | 10/1974 | Zeff | C02F 9/005 210/138 |
| 9,095,633 B1 * | 8/2015 | Dayton | A61L 2/10 |
| 2020/0075972 A1 * | 3/2020 | Jorgenson | A61L 2/16 |

* cited by examiner

*Primary Examiner* — Sean E Conley
(74) *Attorney, Agent, or Firm* — William G. Sykes

(57) ABSTRACT

A lamp appliance for emitting UVC light for disinfection is shown and described. The appliance includes timing controls settable by the user to control time of UVC emission and to provide a delay feature enabling a user to set the controls and exit a vicinity being treated by the lamp prior to UVC being emitted. Manual controls are redundant, including a first general power switch for bringing power to control electronics, and also a second switch initiating UVC emission. The appliance includes an illuminated display to annunciate time settings. The UVC element is pivotal on the chassis, to adjust direction of UVC emission. In one position, the UVC element is shielded to limit UVC emission to a limited size target. A remote controller is provided. The appliance is arranged with its length vertically oriented, to occupy minimal floor space.

10 Claims, 2 Drawing Sheets

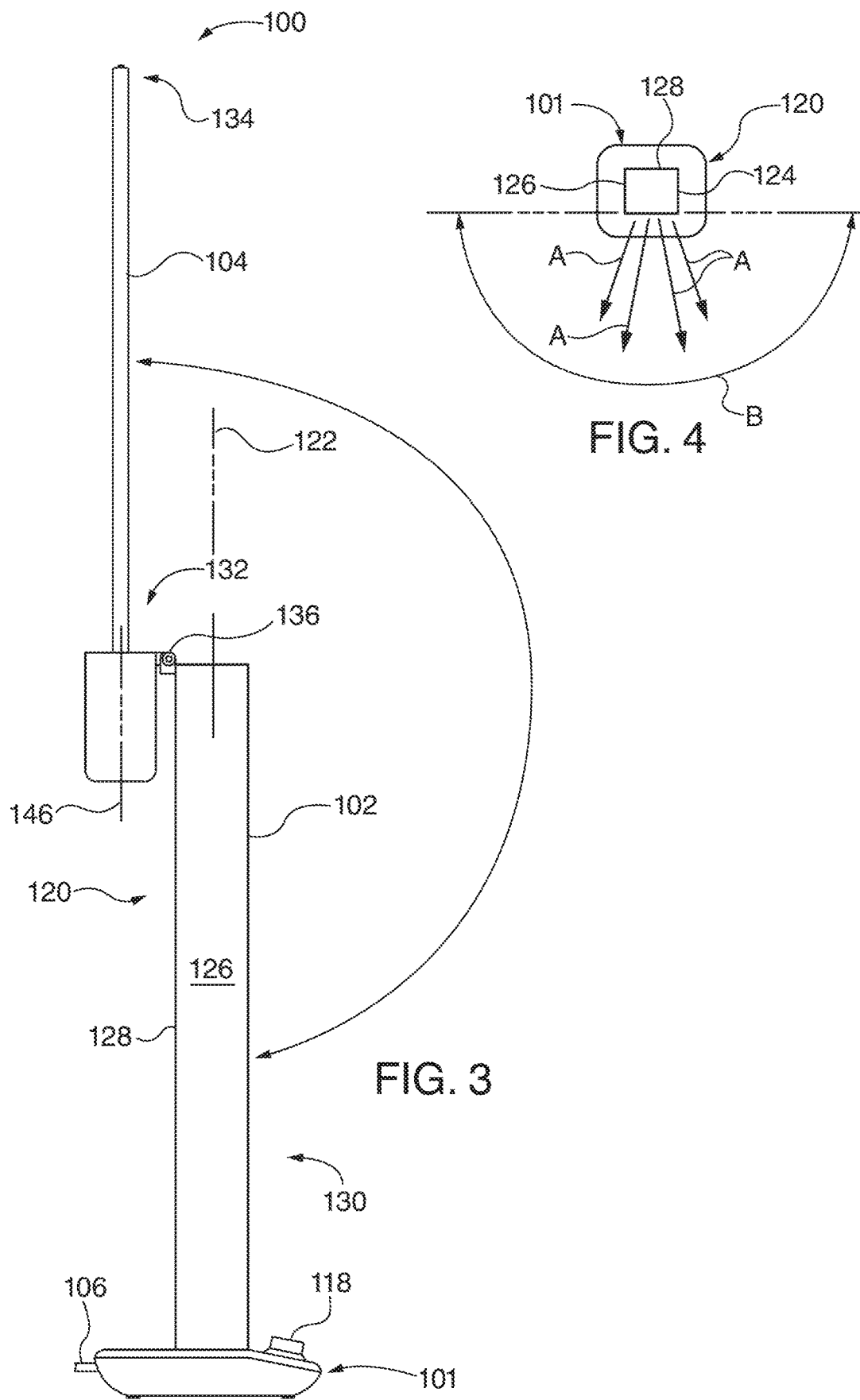

DISINFECTING UVC LAMP APPLIANCE

RELATED APPLICATIONS

This application claims priority in accordance with 37 CF.R. ¶1.19(e) to U.S. Provisional patent Application Ser. No. 63/558,607 filed for DISINFECTING UVC LAMP APPLIANCE filed May 28, 2020 which is included herein in its entirety by reference.

FIELD OF THE DISCLOSURE

The present disclosure relates to drivelines for ventricular assist devices, and more particularly, to a protective sheath for use externally to a patient having a ventricular assist device and associated driveline.

BACKGROUND OF THE INVENTION

This invention relates in general to disinfection via propagation of UVC light, and more particularly, to a lamp appliance for propagating UVC light.

Disinfection, or destruction of microbes, can be accomplished by application of appropriate chemicals or by destructive radiated energy. Chemicals can entail certain drawbacks, such as leaving objectionable residues, requiring expensive or inconvenient replenishment, and damaging environmental objects by chemical reaction therewith.

It is preferable to utilize radiated energy, especially where that can be accomplished using ordinary household electrical power.

In particular, there exists a need for a practical lamp appliance for consumers.

SUMMARY OF THE INVENTION

This invention relates to a lamp appliance particularly suited for temporary or periodic use by consumers. The lamp emits ultraviolet light in the C band, which band is deemed most effective for destruction of microbes in household settings. The lamp appliance connects conveniently to household AC power by plug and cord.

The lamp appliance has timing controls readily settable by the user to control elapsed time of UVC emission. This is a desirable feature in a consumer item due to anticipated needs to avoid unduly cause space within a residential or other human occupied building to be off limits to human traffic due to hazards of UVC light. The timing control includes a delay feature enabling a person to set up the lamp for operation, and to evacuate a space to be treated prior to emission of UVC light. Controls are redundant as a precaution against unintended activation of the UVC element.

The lamp appliance includes an illuminated display for annunciating time settings for operation.

The UVC element is movable to enable advantageous direction of emitted UVC light. In one position, the UVC element is shielded to restrict an emitted UVC beam for focusing on a specific, limited target.

A remote controller is provided with the lamp appliance.

The lamp appliance is arranged so that its length is vertically oriented. The UVC element is fixed to a head pivotally coupled to a vertically oriented body having an enlarged base. Hence the lamp appliance occupies limited floor space, while being versatile in its ability to project UVC light in occupiable building spaces.

Various advantages of this invention will become apparent to those skilled in the art from the following detailed description of the preferred embodiment, when read in light of the accompanying drawings.

BRIEF DESCRIPTION OF THE DRAWINGS

Various features and attendant advantages of a reactive mattress and a pendant controller combination will become more fully appreciated when considered in view of the accompanying drawings, in which like reference characters designate the same or similar parts and/or features throughout the several views, and wherein:

FIG. 3 is a side elevational view of the disinfecting lamp appliance of FIG. 1; and FIG. 4 is a top plan view of the disinfecting lamp appliance of FIG. 1, with minor components omitted for clarity of view.

Drawing FIGS. 1, 3, and 4 are drawn to internal scale, but not necessarily to external scale. By internal scale it is meant that the parts, components, and proportions thereof in the illustrated inventive example are drawn to scale relative to one another. As employed herein, external scale refers to scale of the illustrated example relative to scale of environmental elements or objects shown in the drawings. Where external scale is asserted, the inventive and environmental elements are to scale relative to one another but of course may not be drawn to real or true life scale.

DETAILED DESCRIPTION OF THE PREFERRED EMBODIMENT

The present invention contemplates a portable lamp appliance 100 for emitting UVC light for the purpose of disinfecting habitable portions of buildings (not shown).

Figure 1:
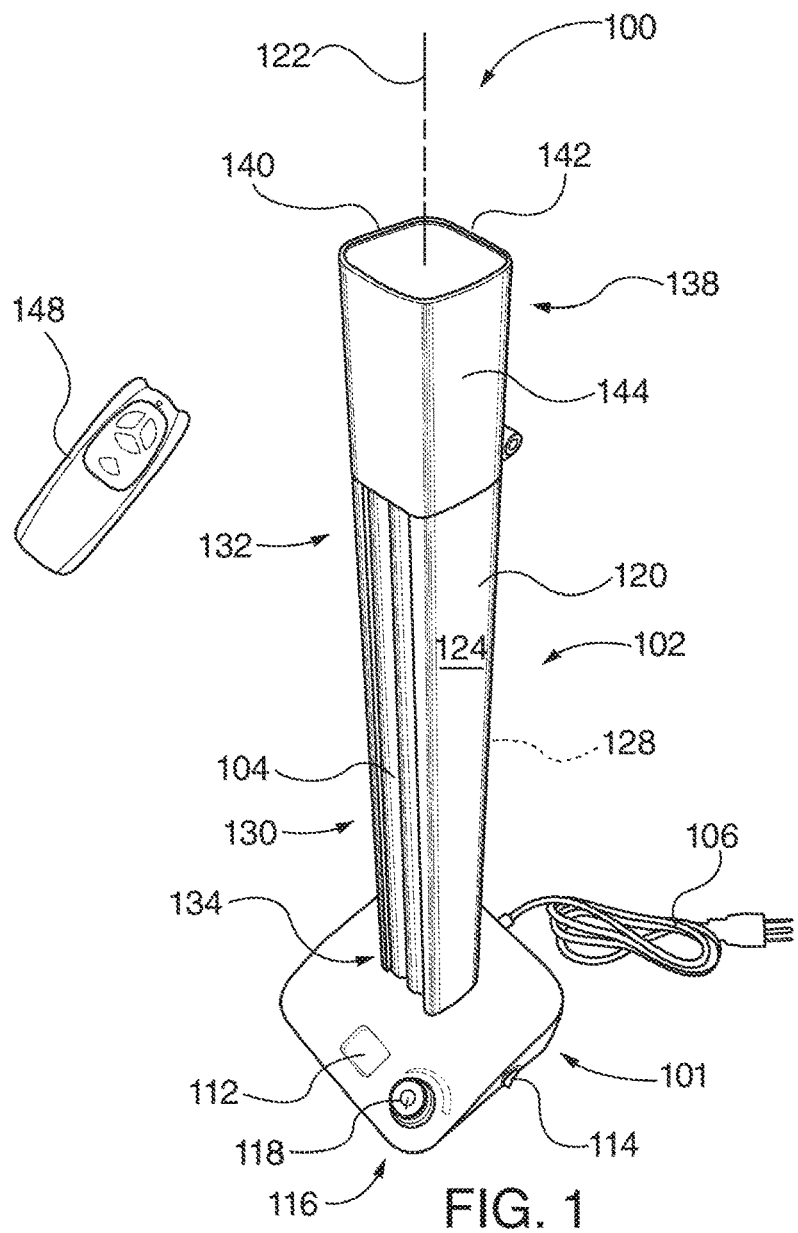
FIG. 1 is a perspective view of a disinfecting lamp appliance, according to at least one aspect of the invention.

Referring now to the drawings, there is illustrated in FIG. 1 a disinfecting lamp appliance 100 suitable for use in occupiable spaces such as residential, office, institutional, industrial, and commercial premises. In a currently preferred embodiment, lamp appliance 100 is twenty-six inches high, seven to eight inches in width and depth (not including a flexible power cord) as taken at a base 101 and weighs three to four pounds.

Figure 2:
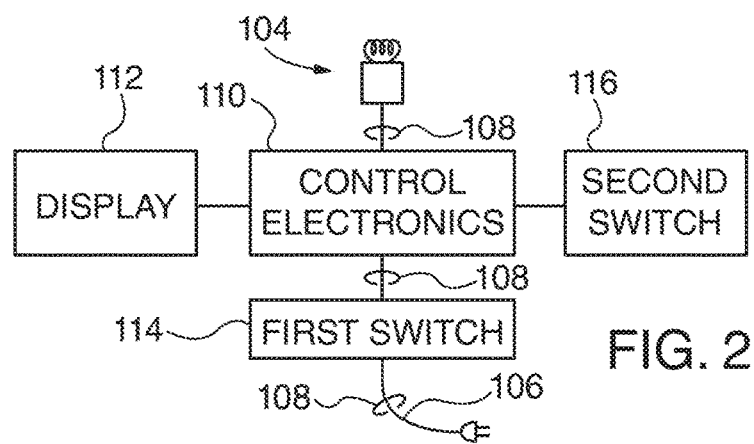
FIG. 2 is diagrammatic representation of an electrical system of the disinfecting lamp appliance of FIG. 1.

Disinfecting lamp appliance 100 comprises a chassis 102, a lamp 104 configured to emit light in an ultraviolet C range of wavelengths. Lamp 104 is supported on chassis 102. Lamp appliance 100 includes an electrical system (shown diagrammatically in FIG. 2) for operating lamp 104. The electrical system may include a power source 106, conductors 108 conducting power from power source 106 to lamp 104, and a switching arrangement controlling access of power from power source 106 to lamp 104. The switching arrangement includes a time delay feature inhibiting illumination of lamp 104 for a predetermined time interval after the switching arrangement is operated to conduct power to lamp 104. The switching arrangement will be understood to include electronic circuitry (represented as control electronics 110 in FIG. 2). It will be understood that power circuitry comprising at least conductors 108, control electronics 110, and connecting signal circuitry which may not be shown will include conventional components to achieve performance as described herein, even though not all components are explicitly shown. The functions described herein are easily achievable by those of skill in the art and need not be specifically described.

The term "appliance" is used herein to distinguish between on one hand, just the light emitting element (lamp 104) and on the other hand, the entire assembly (disinfecting lamp appliance 100) including lamp 104, base 101, chassis 102, the electrical system, etc.

Chassis 102 includes relatively rigid members for supporting electrically powered components. As used herein, "relatively rigid" means that these members, including a housing of base 101 and a shield 120, will not spontaneously deform or slump when not subjected to external forces. Shield partially surrounds and protects lamp 104. Lamp 104 may comprise a single tube or as shown, plural tubes. A longitudinal axis 122 of shield 120 is vertical when base 101 rests on a horizontal environmental surface (not shown).

It should be noted at this point that orientational terms such as vertical and horizontal refer to the subject drawing as viewed by an observer. The drawing figures depict their subject matter in orientations of normal use, which could obviously change with changes in posture and position of the novel accessory mount as mounted on the personal watercraft. Therefore, orientational terms must be understood to provide semantic basis for purposes of description, and do not limit the invention or its component parts in any particular way.

The electrical system comprises a first functionality setting an adjustable run time period during which lamp 104 is illuminated, and a second functionality initiating operation of the time delay feature. After the predetermined time interval has run, the second functionality connects power to lamp 104 for the adjustable run time period and disconnects power from lamp 104 after the adjustable run time period has run or elapsed.

Disinfecting lamp appliance 100 further comprises an illuminable display 112 configured to display a selected adjustable run time period.

The electrical system may further comprise electronic time delay circuitry providing the time delay feature, a first switch 114 controlling power from power source 106 to the electronic time delay circuitry, and a second switch 116 controlling power from the electronic time delay circuitry to lamp 104. Hence redundant control is required to illuminate lamp 104. Control is redundant in that first, first switch 114 must be turned to an "on" position to bring power to the electronic control circuitry, and then power under the constraints of an initial delay and a run time period set by the user is affirmatively controlled using second switch 116.

Unless otherwise indicated, the terms "first", "second", etc., are used herein merely as labels, and are not intended to impose ordinal, positional, or hierarchical requirements on the items to which these terms refer. Moreover, reference to, e.g., a "second" item does not either require or preclude the existence of, e.g., a "first" or lower-numbered item, and/or, e.g., a "third" or higher-numbered item.

The electrical system comprises a first functionality setting an adjustable run time period during which lamp 104 is illuminated, and a second functionality initiating operation of the time delay feature. After the predetermined time delay interval has run, the second functionality connects power to lamp 104 for the adjustable run time period and disconnects power from lamp 104 after the adjustable run time period has run.

Second switch 116 includes a switch operator (e.g., a knob 118 to be manipulated by a user of disinfecting lamp appliance 100), operates the first functionality by one motion applied to the switch operator, and operates the second functionality by a different, second motion applied to the switch operator. For example, pressing knob 118 downwardly starts operation. Rotating knob 118 determines lamp run time interval. Both of these actions can only be undertaken after first switch 114 has been moved to the "on" position.

Referring to FIGS. 1 and 3, lamp 104 is movably supported on chassis 102, thereby enabling the lamp to emit light in the ultraviolet C range of frequencies in plural positions relative to the chassis. Note that shield 120 is closed along its length at a right side 124, a left side 126, and a rear side 128, and open at a front side 130. Lamp 104 is linear and comprises a proximal end 132 and a distal end 134, and is pivotally supported on chassis 102 at a first end (i.e., proximal end 132) of lamp 104. Distal end 134 of lamp 104 can pivot through an arcuate path, as shown in FIG. 3.

Chassis 102 includes shield 120 having longitudinal axis 122, wherein lamp 104 is movable to a retracted position partially surrounded by shield 120 and to plural extended positions wherein lamp 104 is outside shield 120. A hinge 136 has friction characteristics enabling lamp 104 to remain at any selected extended position after being pivoted to the selected position. Hence lamp 104 can be moved to any selected angle between the retracted position and the extended position parallel to the retracted position, and is retained by friction at the selected angle.

Shield 120 has a length (along axis 122) and is open along the length to project emitted ultraviolet C light in a radial pattern relative to longitudinal axis 122. The radial pattern extends less than half of a radial pattern that would result from light projection in the absence of shield 120. This is shown in FIG. 4, where a radial pattern of emitted ultraviolet C light is indicated as arrows A. Arc B indicates half of the potential radial pattern of UVC light emission that would exist in the absence of shield 120. The radial pattern indicated as arrows A is considerably reduced from a full three hundred sixty degree pattern that would theoretically be possible in the absence of shield 120. This restricted pattern is useful in constraining UC light treatment of specific areas of a room (the room is not shown), and can be used to treat areas such as those under counters, desktops, sinks, and the like when it is undesirable to have UVC light bear on other nearby objects.

The electrical system may comprise the first functionality setting the adjustable run time period during which the lamp is illuminated, the second functionality initiating operation of the time delay feature, and illuminatable display 112 configured to display a selected adjustable run time period. Illuminatable display 112 may be located on base 101.

Disinfecting lamp appliance 100 may further comprise a lamp head 138 fixed to lamp 104. Lamp 104 is pivotally anchored at lamp head 139 to shield 120. Lamp head 138 protectively houses a socket for receiving lamp 104 where lamp 104 is removably coupled to disinfecting lamp appliance 100, or alternatively, houses a permanent mechanical and electrical connection, where lamp 104 is a permanent part of disinfecting lamp appliance 100.

Lamp head 138 also provides a convenient handle to be grasped and manipulated when adjusting an extended position of lamp 104.

This avoids hand contact with lamp 104, which hand contact may convey skin oil and other contaminants to lamp 104.

As seen in FIG. 3, lamp 104 is movable to an extended position parallel to the retracted position and pointing oppositely relative to the retracted position. This also elevates lamp 104 on disinfecting lamp appliance 100, enabling a wider, more effective radiation pattern than would be the case if lamp 104 were not movable to such a position.

Recalling that shield 120 includes three sides 124, 126, 128 covering lamp 104 along the length of lamp 104 and that longitudinal axis 122 is a first longitudinal axis centrally located within three sides 124, 126, 128, lamp head 138 comprises three sides 140, 142, 144 each coincident with one of the three sides 124, 126, 128 of shield 120 and a second longitudinal axis 146 (FIG. 3) centrally located within three sides 140, 142, 144 of lamp head 138. In the retracted position, first longitudinal axis 122 is aligned with second longitudinal axis 146, and three sides 140, 142, 144 of lamp head 138 appear as extensions of three sides 124, 126, 128 of shield 120.

Disinfecting lamp appliance 100 may further comprise a hand holdable remote controller 148 configured to implement the first functionality setting then adjustable run time period during which lamp 104 is illuminated, the second functionality initiating operation of the time delay feature, and after the predetermined time interval has run, connecting power to lamp 104 for the adjustable run time period and disconnecting power from lamp 104 after the adjustable run time period has run, and to operate illuminable display 112.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A disinfecting lamp appliance comprising
a chassis;
a lamp configured to emit light in an ultraviolet C range of wavelengths, wherein the lamp is supported on the chassis; and
an electrical system for operating the lamp, the electrical system including
a power source,
conductors conducting power from the power source to the lamp, and
a switching arrangement controlling access of power from the power source to the lamp, the switching arrangement including a time delay feature inhibiting illumination of the lamp for a predetermined time interval after the switching arrangement is operated to conduct power to the lamp; wherein
the lamp is movably supported on the chassis, thereby enabling the lamp to emit light in the ultraviolet C range of wavelengths in plural positions relative to the chassis;
the lamp is linear and comprises a proximal end and a distal end, and is pivotally supported on the chassis at the proximal end of the lamp, and the distal end of the lamp can pivot through an arcuate path;
the chassis includes a shield having a longitudinal axis, wherein the lamp is movable to a retracted position partially surrounded by the shield and to plural extended positions wherein the lamp is outside the shield;
the shield has a length and is open along the length to project emitted ultraviolet C light in a radial pattern relative to the longitudinal axis, and the radial pattern extends less than half of a radial pattern that would result from light projection in the absence of the shield;
the disinfecting lamp appliance further comprising a lamp head fixed to the lamp, and wherein the lamp is pivotally anchored at the lamp head to the shield;
the shield includes three sides covering the lamp along the length of the lamp and the longitudinal axis is a first longitudinal axis centrally located within the three sides; and
the lamp head comprises three sides each coincident with one of the three sides of the shield and a second longitudinal axis centrally located within the three sides of the lamp head, whereby in the retracted position, the first longitudinal axis is aligned with the second longitudinal axis, and the three sides of the lamp head appear as extensions of the three sides of the shield.

2. The disinfecting lamp appliance of claim 1, wherein the electrical system comprises:
a first functionality setting an adjustable run time period during which the lamp is illuminated, and
a second functionality initiating operation of the time delay feature, and after the predetermined time interval has run, connects power to the lamp for the adjustable run time period and disconnects power from the lamp after the adjustable run time period has run.

3. The disinfecting lamp appliance of claim 2, further comprising an illuminable display configured to display a selected adjustable run time period.

4. The disinfecting lamp appliance of claim 1, wherein the electrical system further comprises:
electronic time delay circuitry providing the time delay feature;
a first switch controlling power from the power source to the electronic time delay circuitry; and
a second switch controlling power from the electronic time delay circuitry to the lamp, whereby redundant control is required to illuminate the lamp.

5. The disinfecting lamp appliance of claim 4, wherein
the electrical system comprises a first functionality setting an adjustable run time period during which the lamp is illuminated, and a second functionality initiating operation of the time delay feature, and after the predetermined time interval has run, connects power to the lamp for the adjustable run time period and disconnects power from the lamp after the adjustable run time period has run, and
the second switch includes a switch operator, operates the first functionality by one motion applied to the switch operator, and operates the second functionality by a different second motion applied to the switch operator.

6. The disinfecting lamp appliance of claim 1, wherein the chassis includes a base fixed to the shield, and the longitudinal axis of the shield is vertical when the base rests on a horizontal environmental surface.

7. The disinfecting lamp appliance of claim 6, wherein the electrical system further comprises:
a first functionality setting an adjustable run time period during which the lamp is illuminated;
a second functionality initiating operation of the time delay feature, and after the predetermined time interval has run, connects power to the lamp for the adjustable run time period and disconnects power from the lamp after the adjustable run time period has run; and
an illuminable display configured to display a selected adjustable run time period, wherein the illuminable display is located on the base.

8. The disinfecting lamp appliance of claim 1, wherein the lamp is movable to an extended position parallel to the retracted position and pointing oppositely relative to the retracted position.

9. The disinfecting lamp appliance of claim 8, wherein the lamp can be moved to any selected angle between the retracted position and the extended position parallel to the retracted position, and is retained by friction at the selected angle.

10. The disinfecting lamp appliance of claim 7, further comprising a hand holdable remote controller configured to implement the first functionality setting an adjustable run time period during which the lamp is illuminated, the second functionality initiating operation of the time delay feature, and after the predetermined time interval has run, connecting power to the lamp for the adjustable run time period and disconnecting power from the lamp after the adjustable run time period has run, and to operate the illuminable display.

* * * * *